United States Patent [19]

Thorburn

[11] Patent Number: 4,470,813

[45] Date of Patent: Sep. 11, 1984

[54] HIGH SPEED TURBINE ASSEMBLY FOR DENTAL HANDPIECES AND THE LIKE

[75] Inventor: Fred E. Thorburn, Kirkland, Wash.

[73] Assignee: The J. M. Ney Company, Bloomfield, Conn.

[21] Appl. No.: 451,440

[22] Filed: Dec. 20, 1982

[51] Int. Cl.³ .............................................. A61C 1/05
[52] U.S. Cl. .................................. 433/132; 416/200 R
[58] Field of Search .................. 433/132; 416/200; 415/101

[56] References Cited

U.S. PATENT DOCUMENTS

| | | | |
|---|---|---|---|
| 764,498 | 7/1904 | Poole | 415/101 |
| 3,055,112 | 9/1962 | Borden | 433/132 |
| 3,147,551 | 9/1964 | Seegers | 433/132 |
| 3,432,884 | 3/1969 | Lyszkowski et al. | 416/200 |
| 3,469,318 | 9/1969 | Saffir | 433/132 |
| 3,946,490 | 3/1976 | Sotman et al. | 433/132 |
| 3,952,416 | 4/1976 | Lingenhöle | 433/132 |
| 3,962,789 | 6/1976 | Flatland | 433/132 |
| 4,146,964 | 4/1979 | Lares et al. | 433/132 |
| 4,198,754 | 4/1980 | Lares et al. | 433/132 |

*Primary Examiner*—Robert Peshock

[57] ABSTRACT

A high speed turbine handpiece includes a housing with a turbine wheel chamber and a flow passage for air terminating in a nozzle opening on the periphery of the turbine wheel chamber as well as a discharge passage from the chamber to the exterior of the housing. An integrally formed turbine wheel in the chamber has a hub with two axially spaced sets of vanes extending about its circumference with the blades of one set circumferentially offset from the blades of the other set. The nozzle is aligned with the axial spacing or channel between the sets of vanes and is dimensioned to overlap the adjacent edge portions of the vanes so that air entering through the nozzle impinges on both sets of vanes.

9 Claims, 6 Drawing Figures

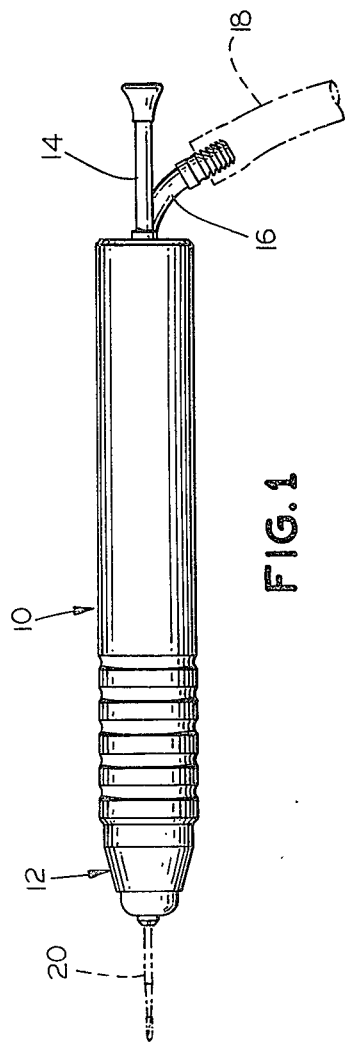
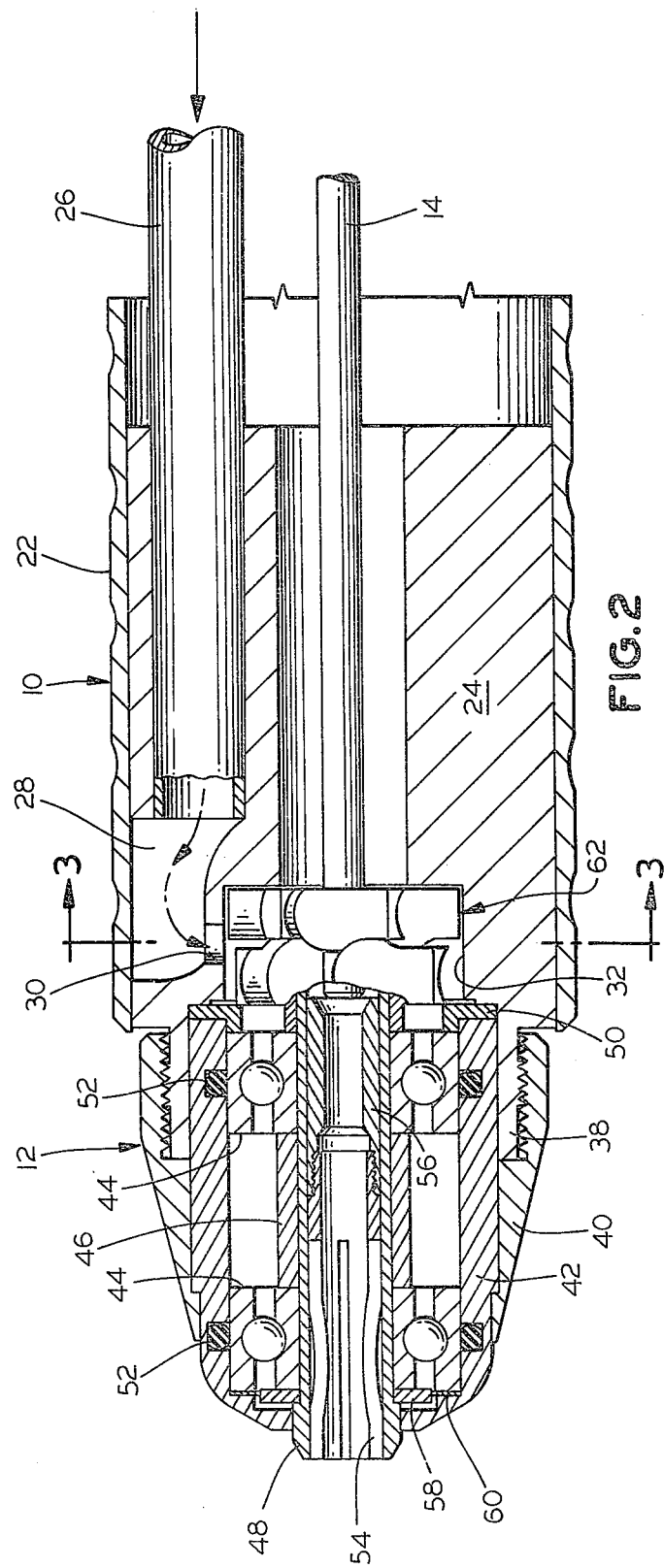

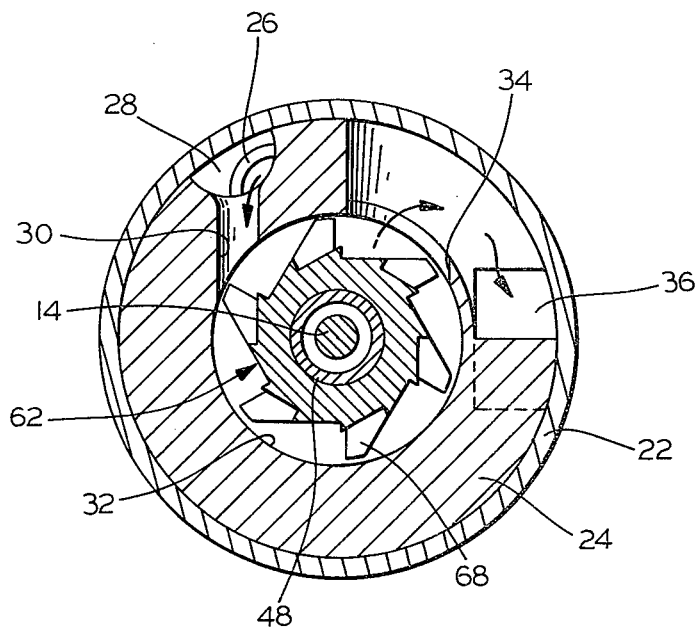
FIG. 3
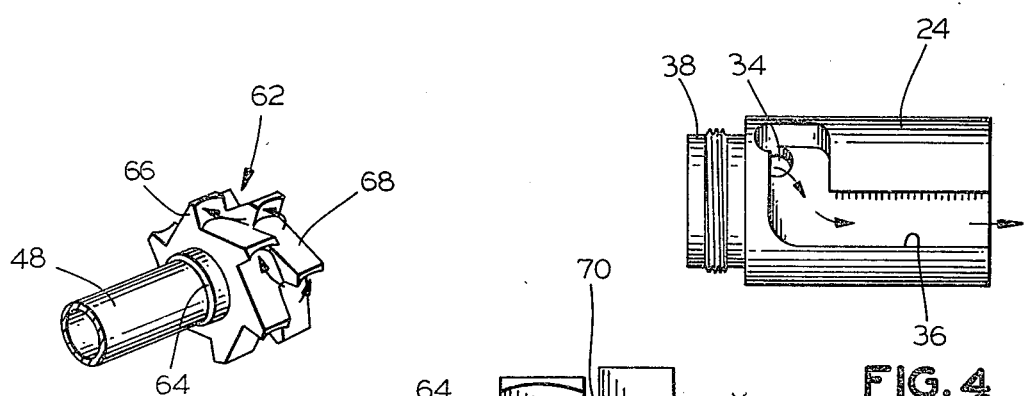
FIG. 5
FIG. 4
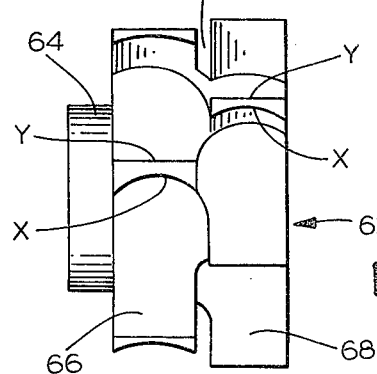
FIG. 6

HIGH SPEED TURBINE ASSEMBLY FOR DENTAL HANDPIECES AND THE LIKE

BACKGROUND OF THE INVENTION

The present invention relates to handpieces which utilize a stream of high pressure air to effect rotation of a tool bit received therein.

Air-driven handpieces are widely employed for effecting oscillation or rotation of a tool bit so as to perform a desired task, either upon a patient or upon a workpiece. Generally, such handpieces utilize a high pressure stream of air acting upon a rotatable or reciprocatable element connected to the tool receiving element to impart the desired motion to the tool bit.

Many of such handpieces utilize a turbine wheel upon which the air stream impinges to effect rotation thereof and thereby effect rotation of a spindle which carries the tool bit. Such handpieces are particularly advantageously used in dental laboratories wherein the tool bit comprises a bur or other abrading tool to facilitate hand shaping of a workpiece.

Among the problems encountered in the use of high speed turbine handpieces of this type are the noise resulting from the air discharge, a tendency for the handpiece to walk along the workpiece due to the angularity of air discharge and low torque at low air velocity.

It is an object of the present invention to provide a novel air powered handpiece to effect rotation of a tool bit, and which provides highly effective and long lived operation.

It is also an object to provide such a handpiece wherein the parts may be readily and relatively economically fabricated and assembled.

Another object is to provide such a handpiece which will operate over a range of velocities in the air feed stream to effect useful rotation of the tool bit mounted therein.

SUMMARY OF THE INVENTION

It has now been found that the foregoing and related objects may be readily attained in a high speed turbine handpiece for effectng rotational motion of a tool bit engaged therein and which utilizes a housing having an inlet fitting for coupling to a source of air under pressure, a turbine wheel chamber, and a flow passage between the fitting and a nozzle opening on the periphery of the turbine wheel chamber. The housing also provides a discharge passage from the turbine wheel chamber and extending from a point spaced about its periphery from the nozzle and to the exterior of the housing.

Rotatable in the chamber is a turbine wheel having a hub and two axially spaced sets of vanes extending about the circumference thereof. The wheel is integrally formed with the blades of one set circumferentially offset from the blades of the other set, and the nozzle is aligned with the axial spacing between the sets of vanes and dimensioned to overlap the adjacent edge portions of the vanes so that air entering through the nozzle impinges directly upon the vanes of each set. A shaft is engaged with the hub of the turbine wheel for rotation therewith, and a tool bit engaging means is carried by the shaft for engaging a tool bit for rotation therewith.

In the preferred embodiment, the trailing edges of the vanes are concave and the faces thereof extend generally radially. The leading edges of the vanes are generally planar and inclined secantally at a relatively shallow angle to intersect the root of the face of the trailing edge of the adjacent vane. The center for the radius of the curve defining the concave face of the vane is located at a point spaced from the plane defined by the adjacent end of the vane, one-fourth of the total distance between the axial ends of the vanes.

Desirably, the vanes of each set are equiangularly spaced, and the vanes of the two sets alternate to define equiangular spacing about the axis of said wheel. This equiangular spacing of the vanes in each set is preferably 60°, and of the two sets combined is 30°. Moreover, the circumferential edges of the vanes are of a thickness substantially less than the width of the nozzle.

The shaft will normally comprise a hollow, generally cylindrical spindle, and the hub has a bore of generally circular cross section extending therethrough dimensioned to seat snugly upon the spindle. The tool bit engaging means is a resiliently expansible chuck means coaxial with and disposed within the bore of the spindle, and the handpiece includes bit releasing means slidably seated within the turbine wheel hub and spindle bore and actuatable externally of the housing to press against the shank of a tool bit seated in the chuck for disengaging the bit therefrom. Desirably, the discharge passage extends generally raidally from a point in the circumference of the turbine chamber and thereafter generally axially in the housing for discharge of the air at the rear end thereof.

BRIEF DESCRIPTION OF THE DRAWINGS

FIG. 1 is a side elevational view of an air turbine handpiece embodying the present invention with a tool bit and air supply hose shown in phantom line;

FIG. 2 is a fragmentary longitudinal sectional view to an enlarged scale of the handpiece and with arrows diagrammatically illustrating air flow;

FIG. 3 is a sectional view thereof along the line 3—3 of FIG. 2 with arrows diagrammatically illustrating air flow;

FIG. 4 is a side elevational view of the core of the housing with arrows indicating air flow through the discharge passage;

FIG. 5 is a perspective view of the turbine wheel as mounted on the fragmentarily illustrated spindle and with arrows diagrammatically showing air flow; and FIG. 6 is an side elevational view of the turbine wheel drawn to an enlarged scale.

DETAILED DESCRIPTION OF THE ILLUSTRATED EMBODIMENT

Turning first in detail to FIG. 1 of the drawings, therein illustrated is a high speed turbine handpiece embodying the present invention which has a housing generally designated by the numeral 10, a bit receiving spindle assembly at the forward end thereof generally designated by the numeral 12, a quick release spindle rod 14 projecting from the rearward end thereof, and an air inlet fitting 16 also projecting from the rearward end. An air hose 18 is shown in phantom line as coupled to the fitting 16, and a tool bit 20 is shown in phantom line as secured in the spindle assembly 12.

As seen in FIGS. 2-4, the housing 10 has a generally cylindrical outer shell 22 and a core 24 seated in the forward end thereof with the shell 22 also forming a cavity therewithin at the rearward end behind the core 24. Seated in the rearward end of the core 24 is one end of the intake air tube 26 which has its other end terminating in the inlet fitting 16. The core 24 has a passage or slot 28 extending from the end of the tube 26 and it opens into the nozzle 30 which is oriented generally tangentially of the turbine wheel chamber 32. Spaced circumferentially about the chamber 32 from the nozzle 30 is the radially oriented exhaust port 34 which opens into the exhaust passage or channel 36 that extends to the rear end of the core 24 where it discharges to the atmosphere. Generally, a fibrous, air-permeable packing (not shown) is provided in the cavity in the rear of the shell 22 to muffle the sound of the air being discharged from the exhaust passage 36.

The forward end of the core 24 has an axially extending neck 38 which is externally threaded to permit engagement thereon of the spindle assembly 12. As seen in FIG. 2, the spindle assembly 12 includes a spindle lock ring 40 which has its inner end internally threaded and engaged on the neck 38 of the core 24.

Trapped within the lock ring 40 by the interfitting shoulders is the spindle housing 42 which has an aperture in its forward end through which extends the generally cylindrical spindle 48. A pair of bearings 44 axially separated by a bearing spacer 46 permit the spindle 48 to rotate freely within the housing 42. The bearings 44 are secured in the assembly by the retainer 50 and O-rings 52, and a bearing protector 58 is disposed at the forward side of the front bearing 44, and a spring washer 60 extends about the outer race thereof.

Seated within the outer end of the spindle 48 is the spring chuck 54, and seated within the inner end thereof is the spindle insert 56. As seen in FIG. 2, the chuck 54 and spindle insert are threadably engaged.

Disposed in the turbine wheel chamber 32 is the turbine wheel generally designated by the numeral 62 and best seen in FIGS. 3, 5 and 6. The turbine wheel 62 has a cylindrical hub 64 which is secured onto the inner end of the spindle 48, and two sets of axially spaced blades 66, 68 extend thereabout with a circumferential valley or channel 70 extending therebetween. Each of the vanes or paddles 66, 68 has a concave face X for its trailing face which lies in a plane extending generally radially of the turbine wheel 62. The opposite or leading face Y of the vanes is rectilinear and slopes secantally at a shallow angle to intersect the adjacent vane at its root.

The concave faces X of the vanes 66, 68 are defined by a radius which is drawn from a center spaced from the adjacent outer edge of the vane about one-fourth the total axial length of the combined vanes. The illustrated embodiment uses six equiangularly spaced vanes 66, 68 in each set, and the vanes of the sets are offset to provide equal spacing, or an angular spacing of 30° about the wheel 62.

The nozzle 30 is centered on the channel 70 between the sets of vanes 66, 68 and is dimensioned so as to extend over the adjacent edge portions so that air entering the chamber 32 impinges directly thereon.

In operation of the illustrated embodiment, an airstream of high velocity is provided from a source (not shown) through the air tube 26 and passage 28, and enters the turbine wheel chamber 32 through the nozzle 30. As it enters the chamber 32, it impinges upon the faces X of the vanes 66, 68 and causes the turbine wheel 62 to rotate. Because the circumferential edges of the vanes 66, 68 are close to the wall of the chamber 32, the bulk of the air stream must zigzag between the vanes of the two sets when the air velocity is greater than the turbine wheel velocity or speed until it reaches the exhaust port 34. However, some flow occurs in the axial spacing or channel 70 therebetween to avoid excessive turbulence and permit some unimpeded circumferential flow.

As the speed of the turbine wheel 62 is slowed, the air flow must again zigzag in its passage to create pressure points on the vanes 66, 68 which helps to maintain the torque as the tool bit is engaged with the workpiece.

Since the air is discharged from the chamber 32 generally radially and at a point spaced circumferentially from the nozzle 30, there is a desirable balancing of the air forces. Moreover, the relatively large cross section of the exhaust port 34 and exhaust passage 36 minimizes forces which would produce a displacing action (or reaction).

The shank of the tool bit 20 is simply inserted into the spring chuck 54 which will provide the necessary engagement to prevent its relative rotation. As the turbine wheel 62 rotates, it effects rotation of the spindle 48 upon which it is mounted and thereby the chuck 54 and tool bit 20 which are at its other end. To effect facile release of the tool bit 20, the spindle release rod 14 is pushed towards the chuck 54. Since it is slidable through the hub 64 and spindle insert 56, it will press against the inner end of the bit 20 and push it outwardly of the chuck 56.

The spindle 48 freely rotates in the bearings 44 of the spindle assembly 14, and the unitary nature of the turbine wheel 62 and spindle/chuck subassembly provides relatively vibration-free operation.

In the illustrated embodiment, two sets of six vanes each are utilized with the vanes being spaced 30° apart about the circumference of the wheel. More or less vanes per set may be employed, but they should be equiangularly spaced for optimum operation.

The width of the channel or spacing between the two sets of vanes should be relatively small but large enough to provide some necessary free circumferential flow. Generally, this width is about 10–25% of the width of a vane, and preferably 15–20%.

The concave faces of the vanes of the turbine wheel are conveniently formed in the workpiece by use of an end mill. The remainder of the vane and channel configuration may be effected by any suitable machining techniques.

Thus, it can be seen from the foregoing detailed specification and drawings that the air turbine handpiece is relatively simple to fabricate and assemble and lends itself to long-lived operation. The handpiece will operate well over a range of air velocities and have a minimized tendency for stalling when the tool bit is engaged with the workpiece. Moreover, the balancing of forces permits facile and accurate handling.

Having thus described the invention, I claim:

1. In a high speed turbine handpiece for effecting rotational motion of a tool bit engaged therein, the combination comprising:

A. a housing having an inlet fitting for coupling to a source of air under pressure, a turbine wheel chamber, a flow passage between said fitting and a nozzle opening on the periphery of said turbine wheel chamber, and a discharge passage from said turbine wheel chamber extending from a point spaced from said nozzle to the exterior of said housing;

B. a turbine wheel rotatable in said chamber and having a hub and two axially spaced apart sets of vanes extending about the circumference thereof and defining a generally annular channel therebetween, said wheel being integrally formed with the blades of one set being circumferentially offset from the blades of the other set, said nozzle being aligned with said annular channel defined by the axial spacing between said sets of vanes and being dimensioned to overlap the adjacent portions of said vanes so that air entering through the nozzle impinges directly upon the vanes of each of said sets;

C. a shaft engaged with the hub of said turbine wheel for rotation therewith; and D. tool bit engaging means on said shaft for engaging a tool bit for rotation therewith.

2. The handpiece of claim 1 wherein the trailing edges of said vanes are concave and the faces thereof extend generally radially, and wherein the leading edges of said vanes are generally planar and inclined secantally at a relatively shallow angle to intersect the root of the face of the adjacent vane.

3. The handpiece of claim 2 wherein the center for the radius of the curve defining said concave faces is located at a point spaced from the adjacent end of the of the vane about one-fourth of the total distance between the axial ends of the vanes.

4. The handpiece of claim 1 wherein said vanes of each set are equiangularly spaced, and the vanes of the two sets alternate to define equiangular spacing of the vanes of said two set about the axis of said wheel.

5. The handpiece of claim 4 wherein said equiangular spacing of each set is 60° and of the two sets is 30°.

6. The handpiece of claim 1 wherein the peripheral edges of said vanes are of a thickness substantially less than the width of said nozzle.

7. The handpiece of claim 1 wherein said shaft comprises a hollow, generally cylindrical spindle, and wherein said hub has a bore of generally circular cross section extending therethrough dimensioned to seat snugly upon said spindle.

8. The handpiece of claim 7 wherein said tool bit engaging means is a resiliently expansible chuck means coaxial with and disposed within said bore of said spindle, and wherein said handpiece includes bit releasing means slidably seated within said turbine wheel hub and spindle bore and actuatable externally of said housing to press against the shank of an associated tool bit seated in said chuck for disengaging the bit therefrom.

9. The handpiece of claim 1 wherein said discharge passage extends generally radially from a point in the circumference of said turbine chamber and thereafter generally axially in said housing for discharge of the air at the rear end thereof.

* * * * *